United States Patent
Jofre Araya (10) Patent No.: US 7,682,151 B2
(45) Date of Patent: Mar. 23, 2010

(54) INTEGRATED SYSTEM TO STABILIZE DENTAL PROSTHESES

(75) Inventor: Jorge Jofre Araya, Concepción (CL)

(73) Assignee: Universidad de Concepcion, Concepcion (CL)

(*) Notice: Subject to any disclaimer, the term of this patent is extended or adjusted under 35 U.S.C. 154(b) by 420 days.

(21) Appl. No.: 11/349,664

(22) Filed: Feb. 8, 2006

(65) Prior Publication Data

US 2006/0194166 A1 Aug. 31, 2006

(30) Foreign Application Priority Data

Feb. 8, 2005 (CL) .................................. 241-2005

(51) Int. Cl.
*A61C 3/00* (2006.01)
*A61C 19/04* (2006.01)

(52) U.S. Cl. .............................. 433/75; 433/72; 433/76; 433/159; 433/160

(58) Field of Classification Search ................. 433/72, 433/75, 76, 159, 160, 172–176
See application file for complete search history.

(56) References Cited

U.S. PATENT DOCUMENTS

| | | | | |
|---|---|---|---|---|
| 5,741,133 | A * | 4/1998 | Gordils et al. ............ | 433/76 |
| 6,319,000 | B1 * | 11/2001 | Branemark ............... | 433/75 |
| 6,716,030 | B1 | 4/2004 | Bulard et al. | |
| 2004/0013999 | A1 * | 1/2004 | Sussman .................. | 433/75 |

OTHER PUBLICATIONS

Adell et al. "A Long-Term Follow-up Study of Osseointegrated Implants in the Treatment of Totally Edentulous Jaws." *JOMI.* vol. 5. No. 4. 1990. pp. 347-359.
Attar et al. "Study of the Effect of Using Mini-Transitional Implants as Temporary Abutments in Implant Overdenture Cases." *Lippincott Williams & amp.* 1999. Abstract Only.
Balkin et al. "Mini-Dental Implant Insertion with the Auto-Advance Technique for Ongoing Applications." *J. of Oral Implantology.* vol. XXVII. No. 1. 2001. pp. 32-37.
Bohsali et al. "Modular Transitional Implants to Support the Interim Maxillary Overdenture." *Compendium.* vol. 20. No. 10. 1999. pp. 975-984.
Jemt et al. "Implant Treatment in Edentulous Maxillae: A 5-Year Follow-up Report on Patients with Different Degrees of Jaw Resorption." *JOMI.* vol. 10. No. 3. 1995. pp. 303-311.
Rodriguez Baciero et al. "Oral Health in the Elderly in Spain." *Ediciones Eguia, S.L.* 1996. pp. 125-131.
Vigolo et al. "Clinical Evaluation of Small-Diameter Implants in Single-Tooth and Multiple-Implant Restorations: A 7-year Retrospective Study." *The International Jr. of Oral & Maxillofacial Implants.* vol. 19, No. 5. 2004. pp. 703-709.

* cited by examiner

*Primary Examiner*—Cris L Rodriguez
*Assistant Examiner*—Heidi M Eide
(74) *Attorney, Agent, or Firm*—Merchant & Gould P.C.

(57) ABSTRACT

The invention discloses an integrated 3 D surgical guide, guide bar, mini-implant system and a procedure to stabilize dental prostheses, based on implanting two parallel mini-implants at a given distance and then joining them by means of a prosthetic bar mounted on them, thus achieving the required strength to mount on the bar a metallic clip that retains a dental prosthesis. The advantage of this integrated system is the stabilization of dental prostheses with high precision and save standardized protocol, lower costs and less trauma for the patient than the traditionally used method.

6 Claims, 7 Drawing Sheets

INTEGRATED SYSTEM TO STABILIZE DENTAL PROSTHESES

The invention discloses an integrated 3D surgical guide, guide bar, mini-implant system and a procedure to stabilize dental prostheses, based on implanting two parallel mini-implants at a given distance and then joining them by means of a prosthetic bar mounted on them, thus achieving the required strength to mount on the bar a metallic clip that retains a dental prosthesis. The advantage of this integrated system is the stabilization of dental prostheses with lower costs and less trauma for the patient than the traditionally used method.

BACKGROUND OF THE INVENTION

A patient that has lost all his/her dental pieces suffers a complex biological, psychological and social disorder that directly affects his/her quality of life. The restitution of these pieces by means of removable prostheses supported on the remaining anatomical structures has been prescribed by more than 200 years, but such restitution is affected by progressive bone mass loss, which makes its stability difficult, especially in the jaw bone.

This causes a high percentage of treated patients to be unable to use their dental prostheses. This situation does not only affect our health system. Studies by Rodriguez-Baciero (Oral Health In The Elderly in Spain, Ed. EGUÍA, Bilbao, Spain, 1996) indicate that 62% of all totally edentulous (toothless) Spanish patients are not able to use their dental prostheses.

Conventional techniques limit the possibilities of treatment for a growing group of people that has serious trouble to develop an appropriate level of life.

The stability of dental prostheses was solved 40 years ago in first world countries with the use of titanium dental implants that anchor them to the bone. Such dental implants have demonstrated their predictable long term success in many studies (Adell et al., Int J Oral Maxillofac Implants, 1990 Winter, 5(4):347-59; Jemt and Lecholm, Int J Oral Maxillofac Implants, 1995 May-June, 10(3):303-11). However, the high cost of these systems, their complexity and the further requirement of multiple clinical stages to install them, and an average treatment duration of 5 months, make this alternative to be out of the scope of public health programs in developing countries.

In the last decade, provisional implants made their appearance in the US market, which has been defined as mini-implants due to their 1.8 mm diameter (versus 3.3 mm in conventional implants).

These implants are very easy to use, require few stages to be installed, have a low cost and are prescribed to provisionally rehabilitate the patient. Conventional implant treatments require 6 to 7 months to be finished, due to the number of clinical stages and the requirement of the implants to heal and to be immobile inside the bone in order to facilitate bone healing around them, which allows resisting bite forces. Inversely, mini-implants start to operate the same day of their insertion to secure provisory prostheses and do not require the patient to be toothless during his/her treatment period.

Unlike definitive implants made of pure commercial titanium (99.75% purity), these little implants comprise a titanium alloy that improves their mechanical strength (90% Ti, 6% Al, 4% V).

In 1998, American odontologist Victor Sendax patented an insertion protocol for a new mini-implant design using some features developed for definitive implants (PAT U.S. Pat. No. 6,716,030). Among them, the contact with the bone is improved, by engraving the titanium surface with citric acid and using a ball-shaped prosthesis retention fixture. These features have made it the only implant to be allowed in USA by FDA to be commercialized as a transitory implant and for semi-permanent treatment (ongoing treatment).

Said implant is hanged from the head using a plastic device and is manually located in the previously prepared place. No incision is required. This causes the recovery time to be shorter and the blood loss during the procedure to be minimal, and also produces a better adaptation of the prosthesis in the same appointment; however, the disadvantage is the total dependence of the insertion of these implants on the ability of the operator and the special care that has to be applied to maintain the implant angle and to allow the bite forces to be parallel to the major axis of the implant. A direction change could cause failure due to excessive force.

Prostheses secured using these implants are immediately mounted on retention capsules (made of silicone) on the rounded head of the implant. This allows a minimal retention of the prosthesis to avoid its movement to cause implant forcing during early bone healing stages; the disadvantage of the system is the requirement of these capsules to be changed at least once every four months to attain proper retention, and also four separate implants have to be inserted to retain one prosthesis.

To these operational difficulties, an important number of in vitro studies add to assess the risk of using implants with such a small diameter, as their small contact area with the bone would receive excessive strain generated by mastication forces that could cause the implant to detach.

The present invention by using a 3D surgical guide, provides a very precise standardized protocol, splinting two of these implants by means of a prosthetic retention bar, in such a way that the total sum of both contact areas with the bone allows to obtain the same results of a large diameter implant, but with more advantages.

To understand more precisely the features and components of this integrated system to establish dental prostheses, it will be described according to the attached drawings without limiting the patent, said drawings being an integral part of the invention, wherein.

DETAILED DESCRIPTION OF THE INVENTION

The integrated system to stabilize dental prostheses of the present invention comprises the following elements: a 3 D surgical guide, a guide bar, an implant holder, two mini-implants and a prosthetic bar.

Figure 1:
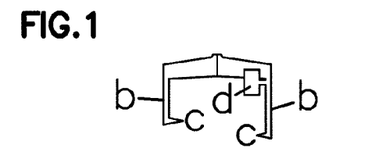
FIG. 1: shows a front view of the 3 D surgical guide.
Figure 2:
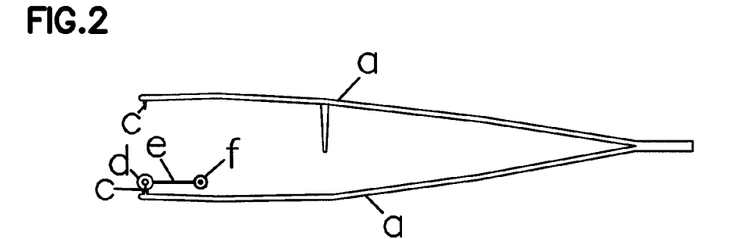
FIG. 2: shows a plan view of the 3 D surgical guide.
Figure 3:
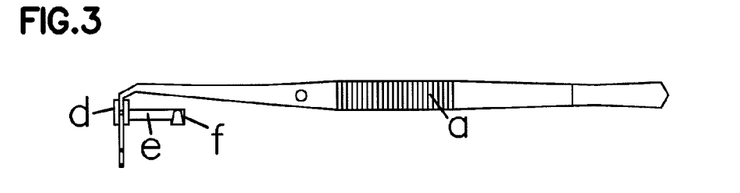
FIG. 3: shows a side view of the 3 D surgical guide.
Figure 7:
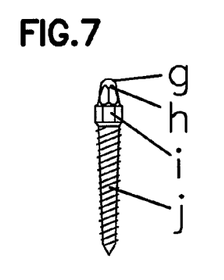
FIG. 7: shows a side view of one of the two mini-implants.
Figure 11:
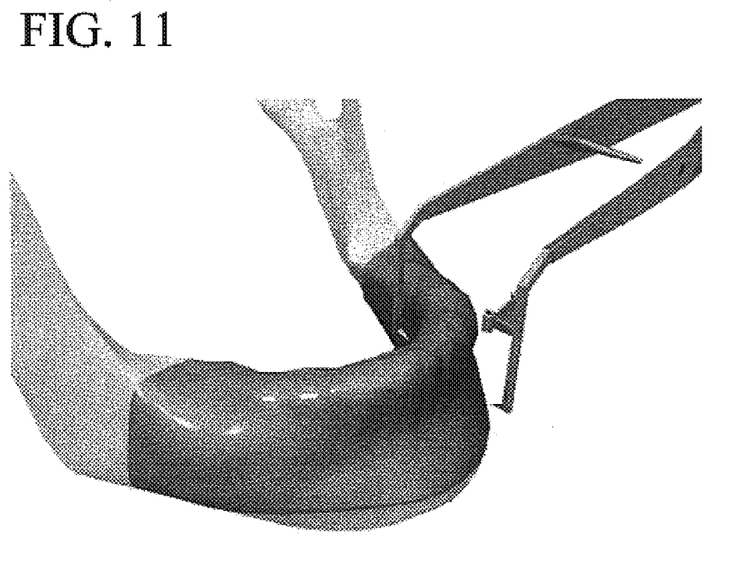
FIG. 11: shows a drawing depicting the introduction of the 3 D surgical guide in the jaw bone.
Figure 12:
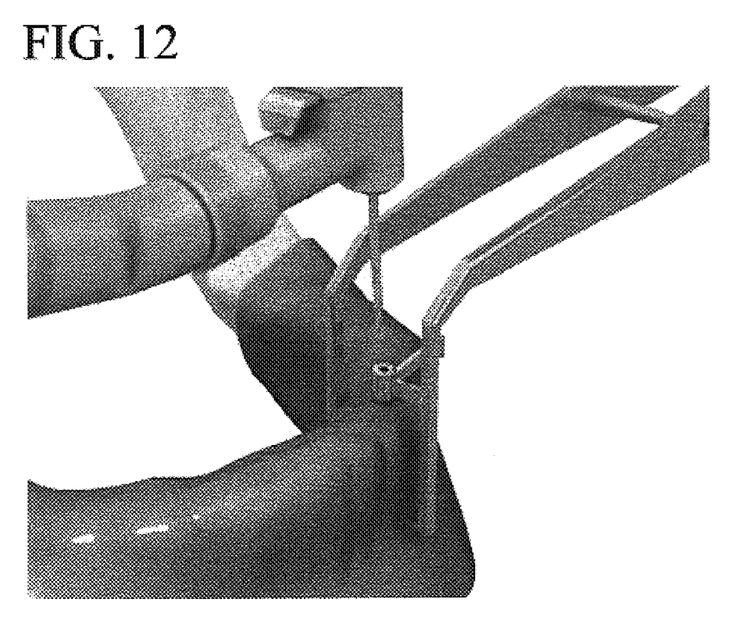
FIG. 12: shows a drawing depicting the 3 D surgical guide inserted in the gum and the drill ready to carry out the first perforation.
Figure 13:
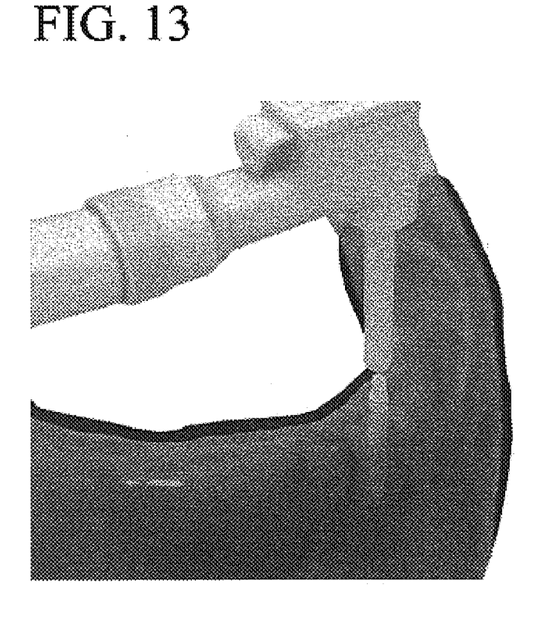
FIG. 13: shows a drawing depicting the insertion of the first mini-implant.

The integrated system to stabilize dental prostheses comprises a 3 D surgical guide (FIGS. 1, 2 and 3) that functions as a positioning guide on the patient's jaw bone (FIG. 11), such 3 D surgical guide being Y-shaped in top and bottom plan view (FIG. 2), its arms (a) having two extensions (b) at their bottom ends that have different heights, with two inwardly positioned nails (c), which are inserted in the lingual and vestibular surfaces of the jaw bone, slightly deviated (approximately 6 mm) from the patient's face middle line, penetrating the gum up to the bone tissue. Moreover, at the end of one of the arms a cylinder (d) having a diameter of 3 mm separates 1 mm inwardly from said arm, said cylinder (d) having a central hole with a diameter of 1 mm and a bar (e) departing from its side in parallel relationship with the arm, said bar having an end cylinder (f) with a trunk-conical perforation inside. The distance between the holes of both cylinders is 11 mm. Subsequently, an initial perforation is made through the hole of the 3 D surgical guide using a drill having a diameter of 1 mm (FIG. 12), and then the first mini-implant (FIG. 7) is inserted centered in the jaw bone in a zone with a minimal bone thickness of 2 mm (FIG. 13).

The mini-implants (FIG. 7) have a structural design that allows immediate bone anchoring, and each of them comprises a trunk-conical top end (g) followed by a base (h) beveled in an angle of 45°, which in turn is followed by a polished cylindrical section (i) having four cuts at its top section that act as anti-rotating elements, said cylindrical section having 2.5 mm of diameter and 2 mm of height and ending in an inverted trunk-conical section (j) with and active surface having 1.8 mm at its largest diameter section, said active surface being double threaded and having variable roughness.

Figure 14:
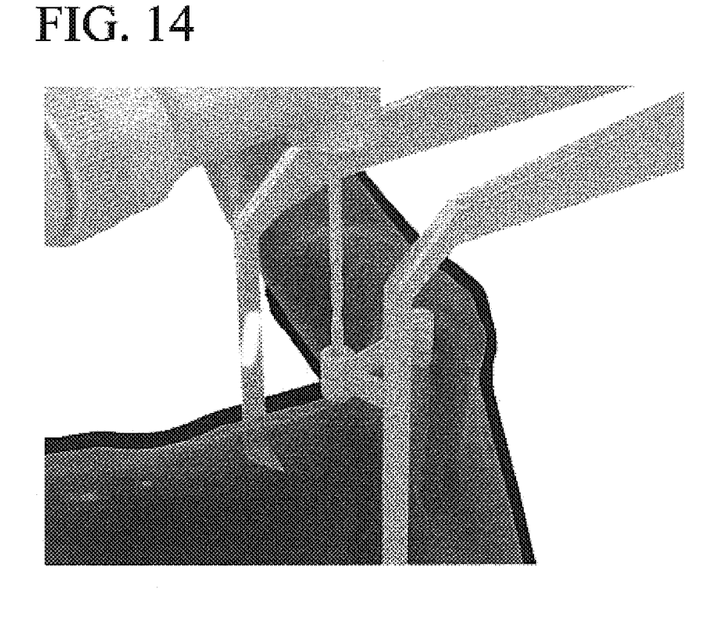
FIG. 14: shows a drawing depicting the course of the second perforation through the 3 D surgical guide.

After inserting the first mini-implant (FIG. 7), the 3 D surgical guide (FIGS. 1, 2 and 3) is repositioned by placing the trunk-conical perforation of the end cylinder (f) on the head of the first mini-implant (g and h), so that bar (e) crosses the patient's middle line and leaves the cylinder with a hole (d) at 11 mm from said first mini-implant. The nails (c) of the jaw are inserted in order to determine the minimal bone thickness and make the second perforation using the drill with a diameter of 1 mm (FIG. 14).

Figure 4:
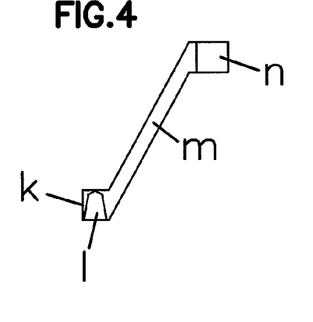
FIG. 4: shows a side view of the guide bar.
Figure 5:
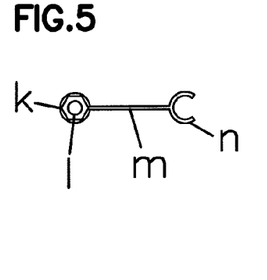
FIG. 5: shows a plan view of the guide bar.
Figure 6:
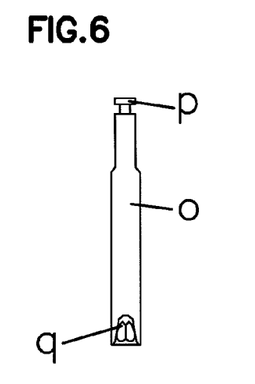
FIG. 6: shows a side view of the implant holder.
Figure 8:
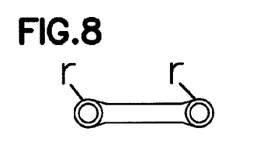
FIG. 8: shows a plan view of the prosthetic bar.
Figure 9:
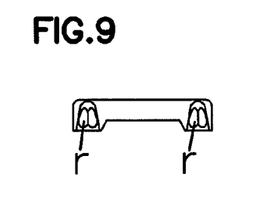
FIG. 9: shows a side view of the prosthetic bar.
Figure 10:
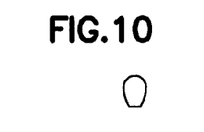
FIG. 10: shows a cross-section of the prosthetic bar.
Figure 15:
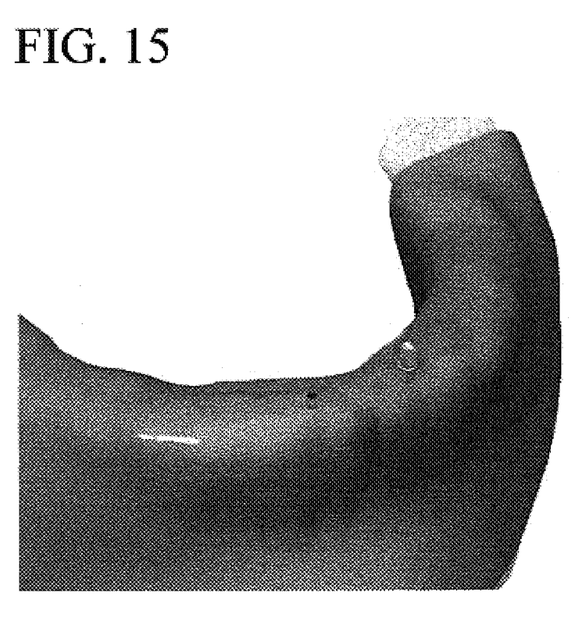
FIG. 15: shows a drawing depicting the second perforation already done at one side of the head of the first mini-implant that has been already inserted.
Figure 16:
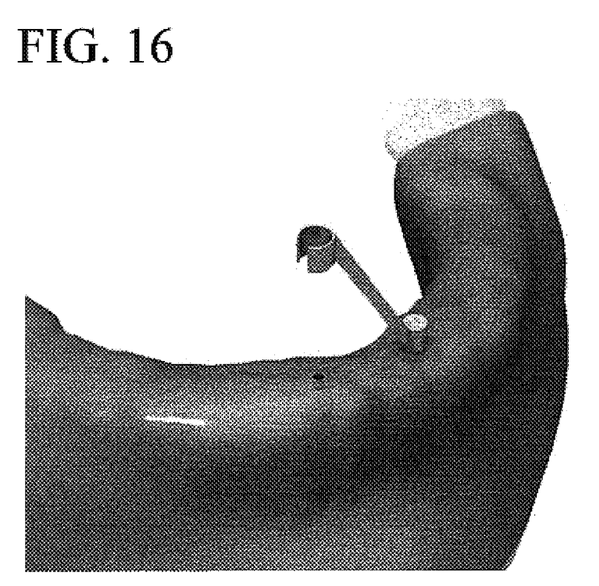
FIG. 16: shows a drawing depicting the guide bar supported on the head of the first mini-implant at its bottom end.
Figure 17:
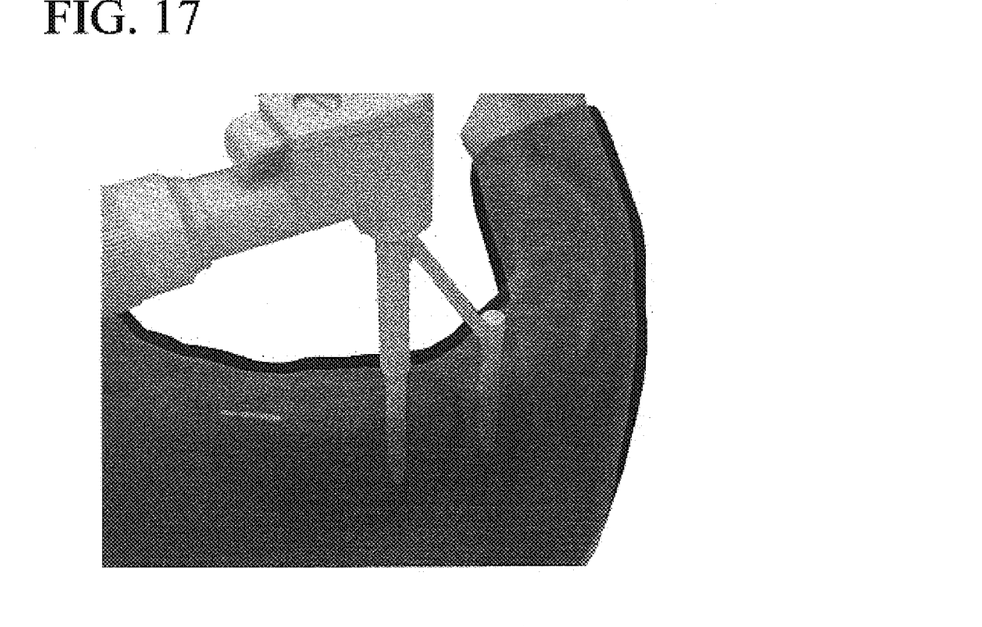
FIG. 17: shows a drawing depicting the insertion of the second mini-implant through the implant holder, said implant holder being connected at its bottom end with the implant installation motor, in addition to being inserted in the open cylinder of the guide bar.
Figure 18:
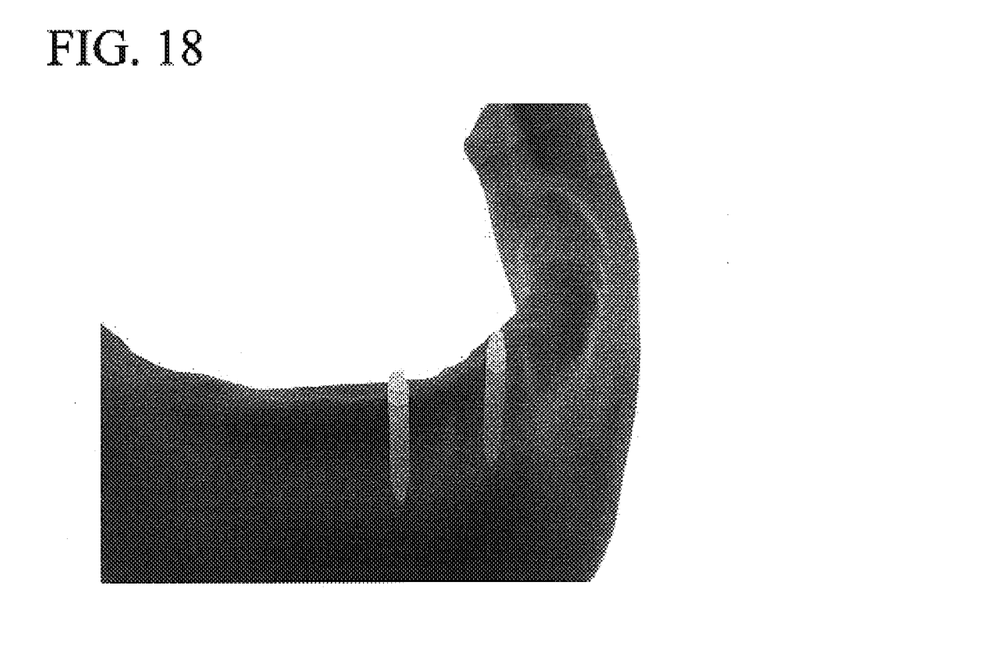
FIG. 18: shows a drawing depicting the heads of the two mini-implants that have been already inserted.
Figure 19:
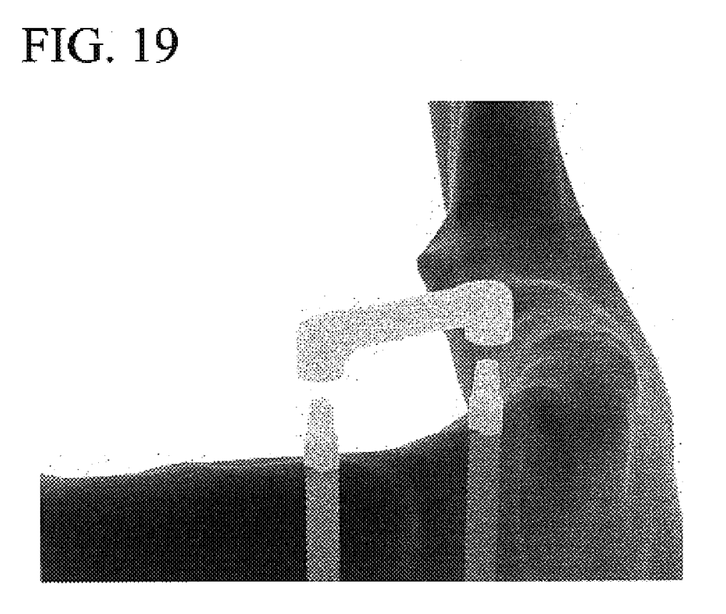
FIG. 19: shows a drawing depicting the prosthetic bar ready to be supported on the heads of both mini-implants.
Figure 20:
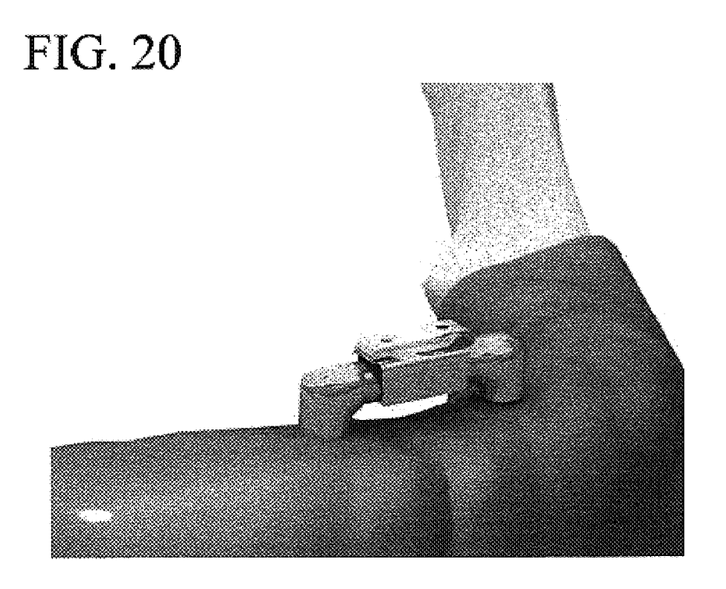
FIG. 20: shows a drawing depicting the prosthetic bar already inserted on the heads of both mini-implants and showing the prosthesis retention hook.
Figure 21:
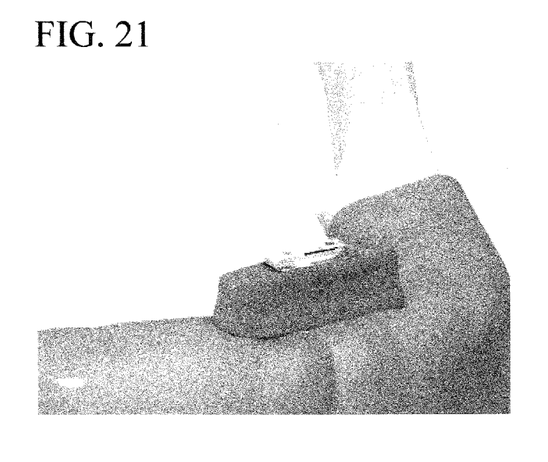
FIG. 21: shows a drawing depicting the rubber-covered prosthetic bar, which leaves uncovered only the retentive flaps of the prosthesis retention hook.
Figure 22:
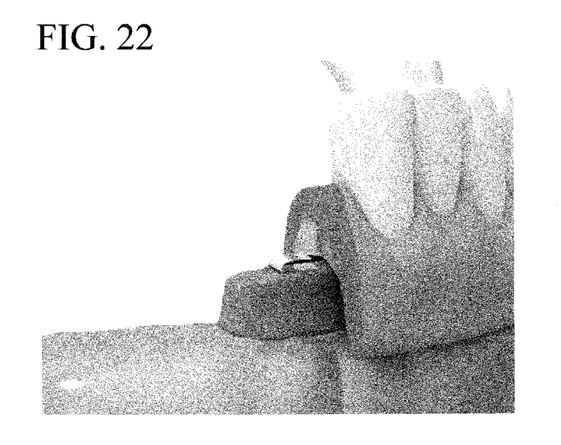
FIG. 22: shows a drawing depicting the implant of the patient's prosthesis on the prosthetic bar.

Once the second perforation has been made (FIG. 15), a guide bar (FIGS. 4, 5 and 16) is introduced in the head of the first mini-implant (g and h), which comprises a bottom cylindrical section (k) inside which a trunk-conical perforation (l) with a shape similar to the shape of the mini-implant head is located, and from the side of said cylindrical section an oblique-ascending bar (m) departs up to 11 mm from the center and up to a height of 15 mm, with a C-shaped open cylindrical end (n) having a length of 3 mm and an internal diameter of 3 mm, which is coincident with the diameter of an implant carrier or implant holder (FIG. 6). Through the open cylinder (n) of the guide bar, an implant carrier or implant holder is introduced, whose total height is approximately 25 mm (FIGS. 6 and 17), to avoid touching the surface of the mini-implant (FIG. 7) that will contact the bone when inserted, said implant carrier or implant holder substantially comprising a cylinder (o) having an external diameter of 3 mm that connects the implant installation motor by means of a cylinder with a smaller diameter (p) at the top end and connects the head of the second mini-implant (g and h) by means of a trunk-conical perforation (q) at the bottom end. After inserting the second mini-implant (FIG. 18), the heads of both mini-implants (g and h) are covered with a resin-based cement and a prosthetic bar is placed on top (FIGS. 8, 9 and 10) joining them together (FIG. 19), said prosthetic bar having a side view with a substantially slanting rectangular shape (FIG. 9) and an ovoid-like cross section (FIG. 10), and its bottom end having two perforations (r) with a distance of 11 mm between their centers and a slightly larger shape than the mini-implant heads, in order to leave enough space for said fixing cement between said perforations and heads. Once the prosthetic bar is installed, a patient's pre-existing prosthesis is adapted and fixed to the retention hooks; for that purpose, the bottom part of said prosthesis corresponding to the bar must be spaced apart and the prosthetic retention hook is secured to the bar (FIG. 20), then the bar is covered with a perforated rubber up to the gum, leaving the retentive flaps of the hook to come out through the perforation and exposing all the hook section that will be secured to the prosthesis (FIG. 21), and finally acrylic resin is added to the prosthesis on the spaced apart section and is placed on the rubber for the hook flaps to be retained on the prosthesis (FIG. 22).

As for the materials that form the parts of the present invention, the following could be stated: the 3 D surgical guide, guide bar, prosthetic bar and mini-implants are made of a Ti6Al4V alloy or tempered surgical steel. The implant holder is an instrument that is commercially available from mini-implant manufacturers, such as the implant holder included in the Sendax MDI mini-implant system kit, from IMTEC Corporation, USA. The cement that joins the heads of the mini-implants and the prosthetic bar is based on any dental resin widely used by odontologists in dental restorations and commercially available, such as Multilink, from IVOCLAR, Shaan, Liechtenstein, or Relix, from 3M, Saint Paul, USA.

Experimental tests carried out in the last four years using these mini-implants have shown that in some cases these mini-implants integrate to the bone as definitive implants, which has been confirmed by histological studies (Balkin, J Oral Implantol, 2001, 27(1):32-7; Bohsali, Compend Contin Educ Dent, 1999, October, 20(10):975-8, 980, 982-3) and clinical reports (Balkin, J Oral Implantol, 2001, 27(1):32-7; el Attar, Implant Dent, 1999, 8(2):152-8; Vigolo 2000 Int J Oral Maxillofac Implants, 2004, September-October; 19 (5):703-9).

In the University of Concepcion, a Finite Element study (mathematical structure analysis) has been performed to compare the strain borne on a single mini-implant (with a diameter of 1.8 mm) versus the strain borne on two mini-implants joined by a rigid bar. The results showed that the contact surfaces of the implants with the bone sum together when the implants are joined, and said summed surface corresponds to a larger diameter implant. The strain limits generated in this joined implant system were largely inferior to risk limits described for conventional implants (having a diameter of 3.75 mm).

Comparatively, the use of a single mini-implant did present a high risk of exceeding the allowed strain limits for bone.

The Advantages of the Present Invention Include:
a) High precision and save standardized protocol
b) Minimal trauma, due to the absence of incision and gum detachment, and also to the minimal requirement of bone tissue and the absence of grafts.
c) Decrease of treatment hours down to two hours in one day, compared with an average of 14 hours in conventional systems, which are distributed in a period reaching up to 6 months.
d) Immediate function and decrease of the treatment period down to one day, compared with conventional systems having a treatment period ranging from 90 to 120 days.
e) Decrease of the need for implements and equipment. An average implementation cost of 217,000 Chilean pesos has been calculated, compared to an average of 4,230,000 Chilean pesos for the implementation of a conventional system.
f) Decrease of treatment costs. A total cost of 89,415 Chilean pesos has been calculated for treatment materials, which is considerably lower than the cost of materials used in a similar treatment using conventional implants that averages 633,271 Chilean pesos.

Application Examples

It was carried out a clinical evaluation of this new design. 75 total edentulous patients were randomized into two intervention groups and one control group (25/group). Inclusion criteria involved no general health disorders, no TMD, and class I Angle. We inserted 50 simultaneous mini-implants (IMTEC, USA) in the edentulous lower jaws of one group of 25 patients, 50 new guided-splinted-mini-implants in another 25 patients, and the last 25 patients acted as the control group, receiving no implants.

After one year in operation, the following parameters were evaluated:

Satisfaction Level

An internationally applied questionnaire known as Goldmann test was applied, allowing classifying the satisfaction in high, medium and poor levels: both the traditional group and the group that used the system of the present invention showed good satisfaction levels regarding their prostheses, after implant insertion, in contrast to the control group.

| Satisfaction level | | Pre-treatment | Post-treatment |
|---|---|---|---|
| Mini-implant System of the present invention | 1 High | 9.5% | 75% |
| | 2 Medium | 76.2% | 25% |
| | 3 Poor | 14.3% | 0% |
| Traditional Implant System | 1 High | 10% | 70% |
| | 2 Medium | 60% | 30% |
| | 3 Poor | 30% | 0% |
| Control | 1 High | 10.5% | 21.1% |
| | 2 Medium | 68.4% | 73.7% |
| | 3 Poor | 21.1% | 5.3% |

Implant Success Level

This is one of the most important parameters in this study, as the success level of implants that carry their prostheses the same day said implants are inserted into the bone (without bone healing period) can be appreciated early. That is, if they fail, it is generally during the first two months.

In the traditional group two implants failed during the first month, giving a success level of 96% for these implants, which is in accordance with described numbers for conventional implants having a diameter of 3.75 mm.

In the group with the implant system of the present invention, none of them have failed. This result has high relevance for the present invention as it is clinical evidence that validates the biomechanical studies or assays.

What is claimed is:

1. An integrated system to stabilize dental prostheses, said integrated system comprising a 3 D surgical guide, a guide bar, an implant holder, two mini-implants and a prosthetic bar, wherein said 3 D surgical guide is Y-shaped in top and bottom plan views, its arms having two extensions at their bottom ends that have different heights, with two inwardly positioned nails, and having at the top end of one of the arms a cylinder with a diameter of 3 mm departing 1 mm inwardly from said arm, said cylinder having a central hole with a diameter of 1 mm and a bar departing from its side in parallel relationship with the arm, said bar having an end cylinder with a trunk-conical perforation inside.

2. An integrated system to stabilize dental prostheses according to claim 1, wherein said guide bar comprises a bottom cylindrical section inside which a trunk-conical perforation with a shape similar to the shape of the mini-implant head is located, and from the side of said cylindrical section an oblique-ascending bar departing up to 11 mm from the center and up to a height of 15 mm, with a C-shaped open cylindrical end having a length of 3 mm and an internal diameter of 3 mm.

3. An integrated system to stabilize dental prostheses according to claim 1, wherein said implant holder comprises a cylinder with an external diameter of 3 mm that connects the implant installation motor by means of a cylinder having a smaller diameter at the top end of said cylinder and connects the head of the second mini-implant by means of a trunk-conical perforation at the bottom end of said cylinder.

4. An integrated system to stabilize dental prostheses according to claim 1, wherein said mini-implants comprise a trunk-conical top end followed by a base beveled in an angle of 45°, which in turn is followed by a polished cylindrical section having four cuts at its top section that act as anti-rotating elements, said cylindrical section having 2.5 mm of diameter and 2 mm of height and ending at an inverted trunk-conical bottom section with an active surface having 1.8 mm at its largest diameter section, said active surface being double threaded and having variable roughness.

5. An integrated system to stabilize dental prostheses according to claim 1, wherein said prosthetic bar comprises a side view with a substantially slanting rectangular shape and an ovoid-like cross section, and its bottom end having two perforations with a distance of 11 mm between their centers, each perforation having 3 mm of depth and a largest diameter of 2.5 mm.

6. A 3 D surgical guide to center bone perforations when a dental prosthesis is installed, wherein said 3 D surgical guide is Y-shaped in top and bottom plan views, its arms having two extensions at their bottom ends that have different heights, with two inwardly positioned nails, and having at the top end of one of the arms a cylinder with a diameter of 3 mm departing 1 mm inwardly from said arm, said cylinder having a central hole with a diameter of 1 mm and a bar departing from its side in parallel relationship with the arm, said bar having an end cylinder with a trunk-conical perforation inside.

* * * * *